United States Patent [19]

Watson et al.

[11] Patent Number: 5,496,264
[45] Date of Patent: Mar. 5, 1996

[54] HEMOSTATIC TRANSDERMAL INJECTION APPLIANCE

[76] Inventors: Robert L. Watson, 1600 Singletree Way, Bowling Green, Ky. 42103; Robert C. Shober, Jr., P.O. Box 143, Alvaton, Ky. 42122

[21] Appl. No.: 259,854

[22] Filed: Jun. 15, 1994

Related U.S. Application Data

[60] Continuation-in-part of Ser. No. 186,280, Jan. 25, 1994, Pat. No. 5,409,466, which is a division of Ser. No. 109,935, Aug. 17, 1993, Pat. No. 5,342,319.

[51] Int. Cl.$^6$ .................................................. A61F 13/00
[52] U.S. Cl. .............................. 602/48; 602/46; 128/888; 604/180
[58] Field of Search ..................................... 604/180, 192, 604/112, 307; 128/888; 602/41, 46, 58, 48

[56] References Cited

U.S. PATENT DOCUMENTS

| | | | |
|---|---|---|---|
| 3,683,911 | 8/1972 | McCormick | 604/180 |
| 3,927,672 | 12/1975 | Garcia | 604/180 |
| 4,294,258 | 10/1981 | Bernard | 128/635 |
| 4,856,504 | 8/1989 | Yamamoto et al. | 128/92 ZW |
| 4,906,240 | 3/1990 | Reed et al. | 602/46 |
| 4,907,579 | 3/1990 | Kum | 602/58 |
| 4,978,342 | 12/1990 | Heimreid | 604/180 |
| 4,985,019 | 1/1991 | Michelson | 604/180 |
| 4,988,341 | 1/1991 | Columbus et al. | 128/888 |
| 5,015,228 | 5/1991 | Columbus et al. | 604/51 |
| 5,037,380 | 8/1991 | Jacobsen et al. | 604/20 |
| 5,086,763 | 2/1992 | Hathman | 128/888 |
| 5,090,406 | 2/1992 | Gilman | 128/888 |
| 5,176,653 | 1/1993 | Metais | 604/167 |
| 5,176,662 | 1/1993 | Bartholomew | 604/283 |
| 5,236,421 | 8/1993 | Becher | 604/180 |
| 5,279,583 | 1/1994 | Shober et al. | 604/198 |
| 5,375,588 | 12/1994 | Yoon | 604/180 |

FOREIGN PATENT DOCUMENTS

| | | | |
|---|---|---|---|
| 2517544 | 6/1983 | France | 604/180 |
| 2451082 | 4/1976 | Germany. | |

OTHER PUBLICATIONS

Rosenberg, A., "Survey Finds Anesthesiologists Are More Cautious, But Risk of Needlestick Remains High in the OR", *Anesthesia Dateline*, pp. 4 and 5, pub. 1992 by Janssen Pharmaceutica Research Foundation.

*Primary Examiner*—John G. Weiss
*Attorney, Agent, or Firm*—Walter C. Farley

[57] ABSTRACT

An elastic, hemostatic appliance for application to the skin of a patient has a first layer of foam material having a proximal surface and a distal surface relative to the patient and an annular layer of foam material having a distal surface adhered to the proximal surface of the first layer, a proximal surface and a central cavity extending entirely through the annular layer. The proximal surface of the annular layer has adhesive for adhering to the skin of the patient. A continuous elastomeric membrane extends across the central cavity adjacent the first layer and closing the distal side of the cavity. A layer of hemostatic material is in the cavity adjacent the membrane, the hemostatic layer having a distal surface against the membrane and a proximal surface exposed through the cavity to a fenestrated membrane so that when the appliance is placed on the skin of a patient with the proximal side of the cavity toward a wound, the annular body inhibits flow of body fluids along the patient's skin and the hemostatic layer encourages hemostasis when contacted by body fluids from the wound. The fenestrated membrane closes the proximal opening of the cavity adjacent the hemostatic layer to promote passage of body fluids to the hemostatic layer. A needle guide with a coupling part at its distal end can be provided for attachment to a mating coupling part of a self-sheathing, retractable needle assembly for closed system injections.

18 Claims, 2 Drawing Sheets

5,496,264

HEMOSTATIC TRANSDERMAL INJECTION APPLIANCE

CROSS-REFERENCE TO RELATED APPLICATIONS

This is a Continuation-in-Part of application Ser. No. 08/186,280 filed Jan. 25, 1994 now U.S. Pat. No. 5,409,466 which is a division of Ser. No. 08/109,935 filed Aug. 17, 1993, now U.S. Pat. No. 5,342,319 which is hereby incorporated by reference.

Devices in accordance with this invention are advantageously used in conjunction with a retractable injection needle assembly disclosed and claimed in U.S. Pat. No. 5,279,583, Shober, Jr., et al, filed Aug. 28, 1992, which is hereby incorporated by reference.

1. Field of the Invention

This invention relates to an appliance for facilitating safer use of a conventional hypodermic needle, or a retractable injection assembly, by protecting the health care provider from accidental contact with the needle, protecting the provider from contact with the blood of a patient, and also facilitating healing of a skin puncture in a patient.

2. Background of the Invention

U.S. Pat. No. 5,279,583 discloses a needle assembly which has the advantage of housing a needle so that the user is protected from accidental puncture with an exposed needle. In that apparatus, a syringe is coupled to a housing which contains the needle and covers it unless intentional steps are taken to cause the point to be exposed after connection to a medication container, a medication delivery apparatus or during intravenous or transcutaneous injection.

However, that invention does not treat the problems associated with exposure of the health care provider with the blood or serum of the patient during or after an injection or blood-drawing procedure. Since contact with the blood or serum of a person infected with certain contagious viruses can be highly dangerous, it is important to avoid such contact.

Normally, before an injection, the area of the skin to be punctured is cleaned with a substance such as alcohol. Following the injection, the needle puncture bleeds to some extent and is typically covered with sterile cotton, sometimes held in place with someone's finger or a small adhesive bandage. A danger exists that accidental contact with the blood emanating from the puncture can occur at that stage of the process. There are numerous other circumstances during blood sampling, administration of medications and liquids or other processes during which such contact can occur to the detriment of the health care provider.

SUMMARY OF THE INVENTION

Accordingly, an object of the present invention is to provide an appliance that permits secure, stable transdermal administration of medication by injection or withdrawal of blood by venous or arterial puncture with a hypodermic needle and eliminates exposure of the health care provider to blood or an exposed needle.

A further object is to provide an improved appliance which includes a puncturable, self-sealing membrane through which an injection needle can be inserted and withdrawn.

Another object is to provide an appliance which is suited for attachment to the skin of a patient to facilitate injection and which can be left on the patient following injection (or withdrawal of blood) until after the puncture site has stopped bleeding.

A still further object is to provide such an appliance which can be provided with a coupling for connection of a retractable needle injection assembly.

Briefly described, the invention comprises an elastic, hemostatic appliance for application to the skin of a patient and includes a first layer of foam material having a proximal surface and a distal surface relative to the patient and an annular layer of foam material having a distal surface adhered to the proximal surface of the first layer, a proximal surface and a central cavity extending entirely through the annular layer. An adhesive on the proximal surface of the annular layer is provided for adhering the annular layer to skin of a patient. A continuous elastomeric membrane extends across the central cavity adjacent said first layer and closes a distal side of the cavity. A layer of hemostatic material is in the cavity adjacent the membrane, the hemostatic layer having a distal surface against the membrane and a proximal surface exposed through the proximal side of the cavity. When the appliance is placed on the skin of a patient with the proximal side of the cavity toward a wound, the annular body inhibits flow of body fluids along the patient's skin and the hemostatic layer encourages hemostasis when contacted by body fluids from the wound.

In addition, the invention can include a fenestrated membrane in the cavity adjacent the proximal side of the hemostatic layer to promote passage of body fluids to the hemostatic layer.

BRIEF DESCRIPTION OF THE DRAWINGS

In order to impart full understanding of the manner in which these and other objects are attained in accordance with the invention, particularly advantageous embodiments thereof will be described with reference to the accompanying drawings, which form a part of this disclosure, and wherein.

DESCRIPTION OF THE PREFERRED EMBODIMENTS

Figure 1:
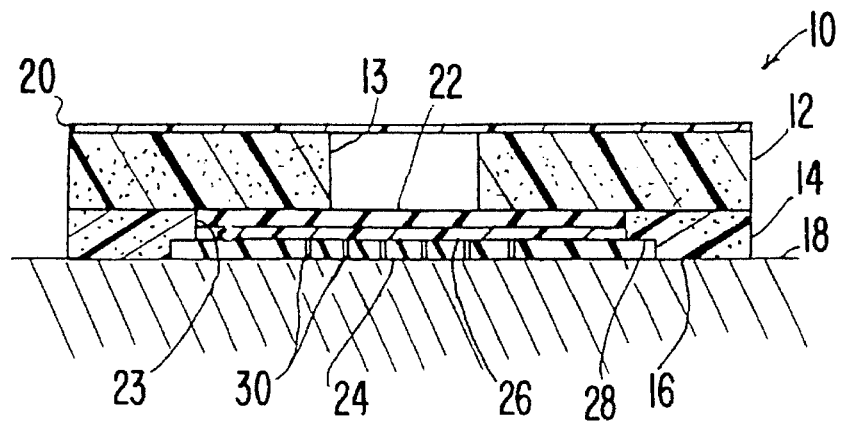
FIG. 1 is an enlarged side elevation, in section, of a first embodiment of an appliance in accordance with the invention, the vertical dimensions thereof being exaggerated.

Referring first to FIG. 1, a first embodiment in accordance with the invention includes a multiple-layer appliance or pad indicated generally at 10 having a distal or outer layer 12 made of an elastic, foamed, closed-cell polymeric material such as polyurethane. In this disclosure, the terms "outer" and "distal" are used interchangeably to mean a portion of the structure of the invention which is farthest away, or faces away, from the skin of a patient, and the terms "inner" and "proximal" are used to mean a portion of the structure which is closest to, or faces toward, the skin of the patient. Layer 12 can be formed with a central opening 13 to provide a visible target area to be penetrated by a hollow needle of a type commonly used for injections or for withdrawing of body fluids such as blood. Opening 13 can be a hole entirely through layer 12 or can be a recess which extends inwardly from the distal surface of layer 12 but does not pass entirely therethrough.

An annular proximal layer 14, also made of an elastic, foamed polymeric material similar to layer 12, has an outer surface which is adhered to the inwardly facing surface of layer 12. A proximal surface 16 of layer 14 is provided with a coating or layer of adhesive for temporary attachment to the skin 18 of a patient, similar to temporary first-aid bandages commonly in use. The distal surface of layer 12 is provided with an easily removable cover 20 to protect the sterility of the structure until use. A similar cover 21, not shown in FIG. 1, is provided to cover surface 16 until that surface is ready to be applied to the skin of the patient.

The central portion of layer 14 is open and defines a generally circular cavity 23 to receive an elastomeric membrane 22 adjacent the proximal surface of layer 12, a fenestrated elastomeric layer 24 and a hemostatic layer 26 between membrane 22 and layer 24. An annular recess 28 extends radially outwardly at the proximal side of layer 14 and the proximal surface of recess 28 has a coating of adhesive to retain membrane 24 with layers 22 and 26 in central cavity 23.

As discussed above, the purposes of the appliance of FIG. 1 are to contain any body fluids which might escape from the body of the patient during injection or taking of samples except for those drawn into a syringe or the like, and also to preliminarily treat a puncture or other wound to promote healing thereof. An "other wound" might be, for example, a nick or cut resulting from presurgical shaving. To accomplish these purposes, the appliance shown in FIG. 1 is adhered to the skin of the patient with the central portion thereof over the wound or the location to be penetrated by a needle.

The layers then perform in the following fashion. Layer 14, which is adhered to the skin around the puncture site, acts as a moisture layer and contains any escaping body fluids within the central space formed in layer 14 and prevents them from escaping laterally along the skin. Layer 24 is fenestrated as symbolized by the illustration of multiple perforations 30 therethrough and encourages passage of blood or sera through to layer 26. Hemostatic layer 26 is or contains a substance such as oxidized regenerated cellulose, a product sold by Johnson & Johnson under the trademark SURGICEL™, and by others, which encourages hemostasis, thereby promoting clotting or formation of a scab over the wound site. In addition, the hemostatic material can be compressed, hemophilic material which expands upon contact with blood. This expansion urges layer 24 toward and against the surface of the skin causing very gentle pressure of the material against the skin, promoting healing thereof.

Elastomeric membrane 22 is a non-coring, self-sealing elastomer which is puncturable by a needle and retains a snug fit around the needle. When the needle is withdrawn from the appliance after administering medication or taking a blood sample, for example, the elastomeric material of membrane 22 wipes most remaining body fluids from the outer surface of the needle, inhibiting and largely preventing escape of those fluids from the appliance.

Figure 3:
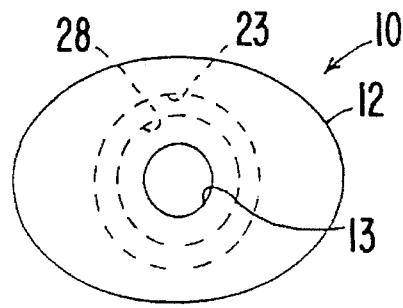
FIG. 3 is a top plan view of the pad of FIG. 1 at a reduced scale.

FIG. 3 shows a top view of the appliance of FIG. 1, at a reduced scale, with cover 20 removed. It will be noticed that the overall shape of the appliance is elongated so as to be elliptical rather than square or circular, and that the materials of layers 12, 22, 24 and 14 are elastic with sufficient elastic memory so that they can be manually elongated and will return substantially to their original dimensions. This permits the pad to be manually elongated very slightly just before applying it to the skin so that, when it is being applied to cover a cut or the like, the elastic forces restoring the pad to its original shape carry the skin with the adhering layer, tending to close the wound and promoting formation of a clot to inhibit further bleeding.

Figure 2:
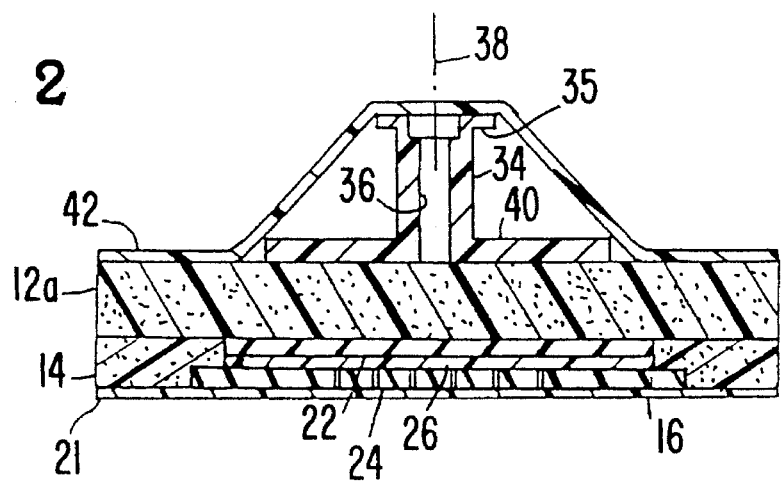
FIG. 2 is an enlarged side elevation, in section, of a second embodiment of an appliance in accordance with the invention, the vertical dimensions thereof being exaggerated.

A further embodiment in accordance with the invention is shown in FIG. 2. In this embodiment, layer 14, membrane 22, and layers 24 and 26 are the same as shown and discussed in connection with FIG. 1, including the formation of cavity 23. A layer 12a is also substantially the same as layer 12 except that it preferably lacks opening 13. In addition, the embodiment of FIG. 3 includes a rigid plastic guide tube 34 having a central lumen 36 dimensioned to slidingly receive a conventional hollow needle along a central axis 38. Tube 36 is unitarily formed with a disk-shaped base 40, the proximal surface of which is adhered to the distal surface of layer 12a. Before use, layer 12a and the tube and base are covered with an easily removable cover 42.

The distal end of tube 34 is preferably provided with flanges 35 forming the male portion of a Luer-Lok® fitting so that a self-retracting needle assembly of the type described in U.S. Pat. No. 5,279,583 having the female portion of such a fitting can be coupled to the tube. This allows the needle to be encased during the entire injection or withdrawal operation. Alternatively, the Luer-Lok® fitting can be used to establish an indwelling cannula placement site for administering fluids or medications.

Figure 4:
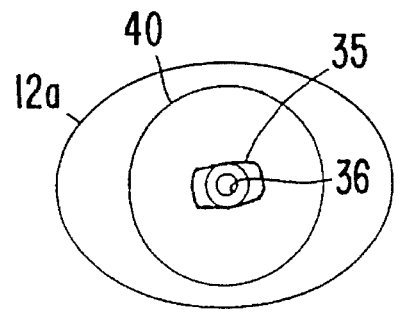
FIG. 4 is a top plan view of the pad of FIG. 2 at a reduced scale.

FIG. 4 shows a top plan view of the embodiment of FIG. 2 from which it will be seen that this embodiment can also have the elliptical shape discussed above for the same reasons.

Figure 5:
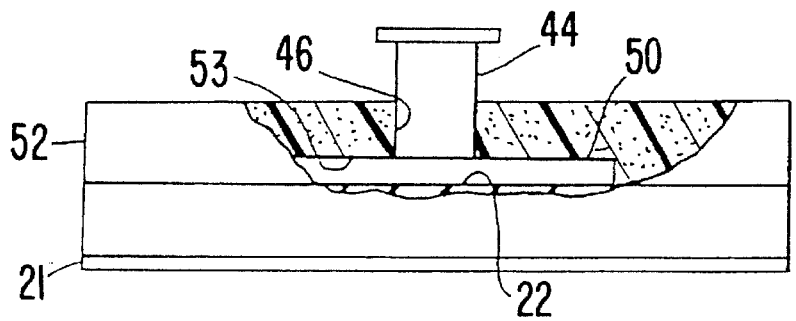
FIG. 5 is a side elevation, in section, of a third embodiment of an appliance in accordance with the invention, the vertical dimensions thereof being exaggerated.

FIG. 5 shows an embodiment of the invention which is similar to that of FIG. 2 but in which a tube 44 is attached to a base 50 and extends through a central opening 46 in a layer 52 which replaces layer 12a. Layer 52 is provided with a cavity 53 in its proximal side to accommodate base 50 so that the base is held between layer 52 and membrane 22. The other layers of the structure are structurally and functionally the same as described in connection with FIG. 2.

Figure 6:
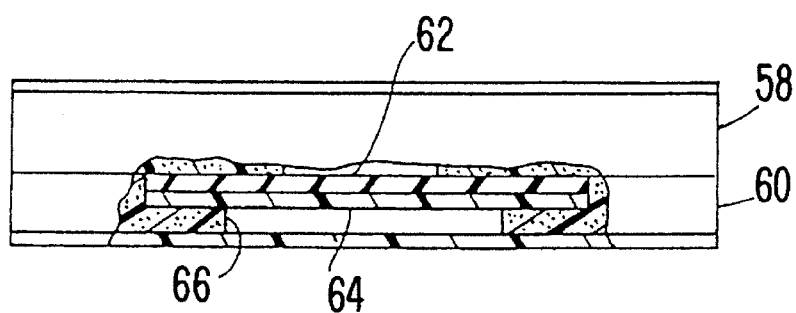
FIG. 6 is a side elevation, in section, of a fourth embodiment of an appliance in accordance with the invention, the vertical dimensions thereof being exaggerated.

From the foregoing discussion it will be recognized that the disclosed embodiments permit injection or sampling of fluids from a body while confining body fluids such as blood or sera so as to protect a medical care-giver while also enhancing cessation of blood flow and promoting healing of a small wound from whatever cause and while also aiding in the protection from accidental puncture from an exposed needle. Its use is therefore beneficial to the patient as well as the care giver. In addition, the embodiment of FIG. 1 is advantageously used as a compressive hemostatic and barrier pad, whether or not used in the context of injection. A further modification of the embodiment of FIG. 1 is shown in FIG. 6 which is similar to FIG. 1 but without the fenestrated membrane. Thus, the top layer 58 is shaped the same as layer 12. The proximate layer 60 is similar to layer 14 but thinner. Layer 60 has a similar cavity to receive an elastomeric membrane 62 adjacent layer 58 and a hemostatic layer 64 which is retained by a lip 66. The appliance of this embodiment can be placed over a wound having the potential for bleeding. The elastomeric membrane 62 acts as a barrier to fluids. In this case, the property of expansion of layer 64 is especially helpful to provide gentle compression which promotes hemostasis.

Figure 7:
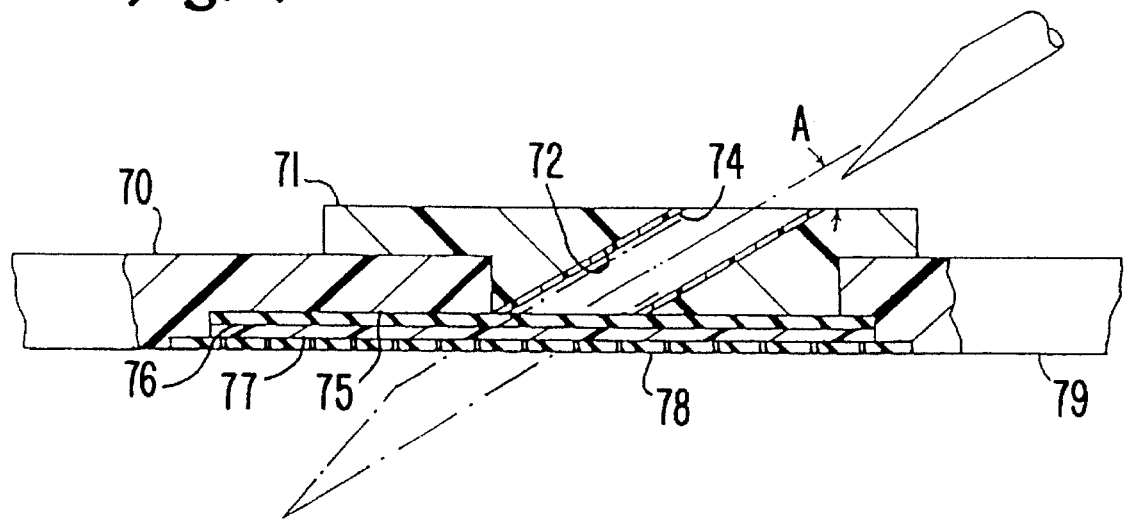
FIG. 7 is a side elevation, in section, of a fifth embodiment of an appliance in accordance with the invention, the vertical dimensions thereof being exaggerated.

A further embodiment is shown in FIG. 7 in which a guide passage is provided at an angle for guiding the needle, especially for blood withdrawal from a vein or artery. This appliance includes a layer 70 of foam material and an insert 71 having a guide passage therethrough, the guide passage having a central axis at an angle A of between about 20° and about 40° from the surface of the insert. Insert 71 can be separately or integrally formed with layer 70 of the same foam material to form a foam body and with a sleeve 74 lining the guide passage, sleeve 74 being of a harder plastic material than the foam.

A cavity or recess extends inwardly from the proximal surface of layer 70 to a back wall 75 and contains a self-sealing elastomeric membrane 76, a layer 77 of hemostatic material and a fenestrated membrane 78 which are arranged and which function in essentially the same manner as layers 22, 26 and 24 of the embodiment of FIG. 1. The proximal surface 79 of the appliance is provided with a layer of adhesive for attachment to the skin of a patient.

The device of FIG. 7 is particularly useful in performing a blood withdrawal procedure on a patient from either a vein or artery. The appliance as described above can be used by passing a phlebotomy needle into the guide passage from the distal end and through the elastomeric layer, hemostatic material and fenestrated layer until the needle protrudes beyond the proximal surface of the annular layer as shown in phantom lines in FIG. 7. The health care provider visually positions the needle at a vein or artery to be penetrated and moves the needle through the skin and into the blood vessel, penetrating into the vein or artery, and proceeds to withdraw blood therefrom in the usual fashion. The health care provider then slides the appliance along the needle toward the patient's skin until the proximal surface of the annular layer is against and adhered to the patient's skin. The needle is then extracted from the patient and from the appliance, leaving the appliance adhered to the patient's skin to contain fluids and promote hemostasis. As described above, membrane 76 wipes the needle as it is extracted and the opening made by the needle reseals, leaving the appliance to seal against the skin to contain fluids and promote hemostasis.

Tube 74 can also be made long enough to protrude from the distal surface of the foam body and can be provided at its distal end with the male portion of a Luer-Lok® coupling, similar to that shown at 35 in FIG. 2, so that a hypodermic needle or other device with the other portion of the coupling can be coupled thereto.

While certain advantageous embodiments have been chosen to illustrate the invention, it will be understood by those skilled in the art that various modifications can be made therein without departing from the scope of the invention as defined in the appended claims.

What is claimed is:

1. An hemostatic appliance for application to the skin of a patient comprising the combination of a first layer of foam material having a proximal surface and a distal surface relative to the patient;

an annular layer of foam material having a distal surface adhered to said proximal surface of said first layer, a proximal surface and a central cavity extending entirely through said annular layer;

adhesive means on said proximal surface of said annular layer for adhering said annular layer to skin of a patient;

a continuous elastomeric membrane extending across said central cavity adjacent said first layer and closing a distal side of said cavity; and a layer of hemostatic material in said cavity adjacent to said membrane, said hemostatic layer having a distal surface against said membrane and a proximal surface exposed through a proximal side of said cavity whereby, when said appliance is placed on the skin of a patient with said proximal side of said cavity toward a wound or puncture site, said annular layer of foam forms an adherent seal with the skin of the patient and inhibits flow of body fluids along the patient's skin, thereby encouraging flow of said fluids to said hemostatic layer so that said hemostatic layer encourages hemostasis.

2. An appliance according to claim 1 and further comprising a fenestrated membrane in said cavity adjacent the proximal side of said hemostatic layer to promote passage of body fluids to said hemostatic layer.

3. An appliance according to claim 2 wherein said first and annular layers are made of a closed cell foam to act as a barrier to blood and other body fluids.

4. An appliance according to claim 2 wherein said elastomeric membrane is made of a non-coring, self-sealing elastomer penetrable by a hypodermic needle whereby, when a needle passes therethrough and is extracted, body fluids remaining on said needle are wiped therefrom by said membrane and said membrane recloses an opening made by said needle to constitute a fluid barrier.

5. An appliance according to claim 4 and further comprising a needle guide attached to said first layer for guiding a hypodermic needle into and through said appliance and to the skin of the patient.

6. An appliance according to claim 2 wherein said hemostatic material expands toward the patient's skin when exposed to blood from a wound in the patient's skin and applies pressure to the wound, thereby promoting hemostasis.

7. An appliance according to claim 1 and further comprising a needle guide attached to said first layer for guiding a hypodermic needle into and through said appliance and to the skin of the patient.

8. An appliance according to claim 7 wherein said needle guide comprises a guide tube having a proximal end and a distal end and means at said distal end for coupling said tube to a retractable, self-sheathing injection device.

9. An appliance according to claim 8 wherein said needle guide includes a generally circular base having a central opening, said base being attached to said proximal end of said guide tube, said base being adhesively attached to said distal surface of said first layer.

10. An appliance according to claim 8 wherein said needle guide includes a generally circular base having a central opening, said base being adhesively attached to said proximal surface of said first layer adjacent said elastomeric membrane, said guide tube extending through said first layer.

11. An appliance according to claim 8 and including first and second covers removably adhered to said distal surface of said first layer and said proximal surface of said annular layer, respectively, to cover said surfaces, said cavity and said guide tube, said covers being removable for use of said appliance.

12. An appliance according to claim 7 wherein said needle guide comprises a guide tube having a proximal end, a distal end and a central axis, said central axis forming an angle of less than 90° with said first layer.

13. An appliance according to claim 12 wherein said angle is between about 20° and about 40°.

14. An appliance according to claim 13 wherein said angle is about 30°.

15. An appliance according to claim 2 and including first and second covers removably adhered to said distal surface of said first layer and said proximal surface and said cavity of said annular layer, respectively, to cover said surfaces, said covers being removable for use of said appliance.

16. An appliance according to claim 2 wherein each said layer is elastic and has sufficient elastic memory to return to substantially its pre-stretched dimensions whereby said appliance can be manually stretched before application to the patient's skin so that the elastic memory tends to compress together edges of a wound or puncture.

17. A method of performing a blood withdrawal procedure on a patient comprising the steps of providing an appliance having a body of foam material having a proximal surface and a distal surface relative to the patient, a central recess extending inwardly from the proximal surface to a back wall, an adhesive on the proximal surface of the body for adhering the appliance to the skin of a patient, a continuous elastomeric membrane extending across the central recess adjacent the back wall and closing a distal side of the cavity, a layer of hemostatic material in the cavity adjacent the membrane, and a needle guide passage extending from the distal surface to the elastic membrane and having a distal end and a proximal end relative to the patient, in sequence, passing a needle into the guide passage from the distal end and through the elastomeric membrane and hemostatic material until the needle protrudes beyond the proximal surface of the foam body, visually positioning the needle at a vein or artery to be penetrated, penetrating the vein or artery, withdrawing blood therefrom, sliding the appliance along the needle until the proximal surface of the annular layer is against and adhered to the patient's skin, and extracting the needle from the appliance, leaving the appliance adhered to the patient's skin to contain fluids and promote hemostasis.

18. A method according to claim 17 wherein the appliance further includes a fenestrated elastomeric layer on the proximal side of the hemostatic material and the step of passing a needle through the passage includes passing the needle through the fenestrated layer.

* * * * *